(12) United States Patent
Auger et al.

(10) Patent No.: US 10,898,403 B2
(45) Date of Patent: Jan. 26, 2021

(54) DEVICE AND METHODS FOR MOVEMENT ASSISTANCE

(71) Applicant: Purdue Research Foundation, West Lafayette, IN (US)

(72) Inventors: Joshua David Auger, Fort Wayne, IN (US); Anna Kacius, Dyer, IN (US); Patrick Miner, Indianapolis, IN (US); Kevin Kral, Lexington, KY (US); Trevor Lear, O'Fallon, IL (US)

(73) Assignee: Purdue Research Foundation, West Lafayette, IN (US)

( * ) Notice: Subject to any disclaimer, the term of this patent is extended or adjusted under 35 U.S.C. 154(b) by 684 days.

(21) Appl. No.: 15/424,269

(22) Filed: Feb. 3, 2017

(65) Prior Publication Data

US 2017/0231853 A1 Aug. 17, 2017

Related U.S. Application Data

(60) Provisional application No. 62/291,846, filed on Feb. 5, 2016.

(51) Int. Cl.
*A61F 5/01* (2006.01)
*A61H 3/00* (2006.01)
(Continued)

(52) U.S. Cl.
CPC ............... *A61H 3/00* (2013.01); *A61F 2/60* (2013.01); *A61F 2/68* (2013.01); *A61F 5/0102* (2013.01); *A61F 5/0123* (2013.01); *A61F 5/0125* (2013.01); *A61F 5/0195* (2013.01); *A61H 1/0229* (2013.01); *A61F 2005/0172* (2013.01); *A61F 2005/0197* (2013.01); *A61H 2201/0165* (2013.01); *A61H 2201/0192* (2013.01);
(Continued)

(58) Field of Classification Search
CPC .... A61H 3/00; A61H 3/008; A61H 2003/005; A61F 5/0123; A61F 5/0125; A61F 5/0102; A61F 5/0195; A61F 2005/0179; A61F 2005/016; A61F 2002/6657
See application file for complete search history.

(56) References Cited

U.S. PATENT DOCUMENTS 5,078,128 A * 1/1992 Grim ..................... A61F 5/0127
602/23
2011/0319801 A1* 12/2011 Ital ....................... A61F 5/0102
602/23

(Continued)

*Primary Examiner* — Kari K Rodriquez
(74) *Attorney, Agent, or Firm* — Hartman Global IP Law; Gary M. Hartman; Domenica N. S. Hartman

(57) ABSTRACT

Assistive movement devices and methods therefor are provided that are capable of redirecting loads from an individual's foot to hip when an individual is recovering from an injury at or below the knee. The devices include a frame assembly comprising an upper member, a lower member, and a joint therebetween. An upper attachment is secured to the upper member and is configured to be secured to the thigh of the individual's leg, and a lower attachment is secured to the lower member or the base and is configured to be secured to a portion of the leg below a knee thereof. A base is secured to the lower member and is configured to support a foot of the leg, and the device adjustably redirects at least a portion of a load resulting from the individual standing and walking from the base to the upper attachment.

11 Claims, 16 Drawing Sheets

(51) Int. Cl.
  *A61F 2/68* (2006.01)
  *A61F 2/60* (2006.01)
  *A61H 1/02* (2006.01)

(52) U.S. Cl.
  CPC .. *A61H 2201/164* (2013.01); *A61H 2201/165* (2013.01); *A61H 2201/1676* (2013.01)

(56) References Cited

U.S. PATENT DOCUMENTS

2013/0035623 A1* 2/2013 Nace .................... A61F 5/0123
  602/16
2016/0175180 A1* 6/2016 Bond ....................... A61H 3/00
  602/23

* cited by examiner

DEVICE AND METHODS FOR MOVEMENT ASSISTANCE

CROSS REFERENCE TO RELATED APPLICATIONS

This application claims the benefit of U.S. Provisional Application No. 62/291,846, filed Feb. 5, 2016, the contents of which are incorporated herein by reference.

BACKGROUND OF THE INVENTION

The present invention generally relates to medical devices. The invention particularly relates to an assistive movement device for individuals suffering from leg injuries at or below the knee.

The 2011 U.S. trauma industry statistics release showed that 864,445 people suffered from fractures requiring crutches. Of those, 318,977 occurred at or below the knee (encompassing ankle, foot, tibia, fibula, and knee injuries). After an operation or other procedure to correct a fracture, the limb is generally set in a protective cast and the individual must use axillary or lofstrand (forearm) crutches for movement. However, injured individuals generally must gradually apply weight to the injured leg in order for the bone to fully heal. Currently, patients may be instructed to transition from the cast into a boot and initially only perform "toe-touch" motions while walking in order to apply a small load on the injured limb. From there, the patient may begin to perform "heel-to-toe" motions and it is up to each individual to control the comfort level with which they balance loading on the injured leg.

These conventional treatments, which rely on crutches to minimize the load on an injured leg during movement, prevent the user from regaining a normal gait in a continuous manner and instead divide up rehabilitation into several separate steps that may result in extension of the time necessary for full recovery of the injured leg. Accordingly, there is an ongoing desire for rehabilitative treatments and assistive movement devices capable of limiting the load on an injured limb while providing the ability for the individual to move with a normal gait.

BRIEF DESCRIPTION OF THE INVENTION

The present invention provides assistive movement devices and rehabilitative treatments that use such devices to redirect loads from the foot to the hip while providing full mobility of the knee, such that an individual recovering from an injury below the knee may walk with a substantially normal gait.

According to one aspect of the invention, an assistive movement device for attachment to the leg of an individual is provided that includes a frame assembly comprising an upper member, a lower member, and a pivoting joint therebetween. An upper attachment is secured to the upper member and has means for securing the upper member to the thigh of the individual's leg. A base is secured to a distal end of the lower member oppositely disposed from the joint and is configured to support a foot of the leg. A lower attachment is secured to the lower member or the base and has means for securing the lower member or the base to a portion of the leg below a knee thereof. Means is provided for adjustably redirecting at least a portion of a load resulting from the individual standing and walking on a surface wherein the portion of the load is redirected from the base to the upper attachment through the upper member, the pivoting joint, and the lower member.

According to another aspect of the invention, a method is provided for assisting mobility of an individual having an injury at or below the knee of a leg of the individual. The method includes providing an assistive movement device having a frame assembly comprising an upper member, a lower member, a pivoting joint therebetween, and a base secured to a distal end of the lower member oppositely disposed from the joint. The upper member of the frame assembly is secured to a first portion of the leg above the knee, the lower member of the frame assembly or the base is secured to a second portion of the leg below the knee, and a foot of the leg is supported by the base. As the individual stands or walks on a surface with the device secured to the leg, the device adjustably redirects at least a portion of a load that results from the individual standing or walking from the base to the to the first portion of the leg through the upper member, the pivoting joint, and the lower member.

Technical effects of the assistive movement device and method described above preferably include the ability to allow an individual to walk with a relatively normal gait on an injured leg while the device adjustably redirects at least a portion of the individual's weight to the hip of the injured leg, such that a limited but controllable load can be applied to the injured leg below the knee.

Other aspects and advantages of this invention will be further appreciated from the following detailed description.

DETAILED DESCRIPTION OF THE INVENTION

Current medical research indicates that bone, tendons, and ligaments may experience improved healing efficiency if placed under loads (known as dynamization) during healing from an injury, nonlimiting examples of which include fractures, soft tissue injuries, and impairments. In view of this research, the present invention generally provides an assistive movement device that is believed to promote an improved recovery process for individuals who have sustained an injury at or below the knee by providing the ability to adjust the amount of load experienced by the injured area (tissue), and particularly the portion of the leg below the knee, when the individual attempts to walk. For convenience, the device 10 will be described hereinafter in relation to a human leg, which herein is referred to in a general use of the term to include the entire lower extremity or limb. Various portions of the leg will generally be described as the thigh (between the hip and knee), the knee, the lower leg (between knee and ankle, known as the cnemis or crus) including the shin (front of lower leg) and the calf (back of lower leg), the ankle, and the foot.

Figure 1:
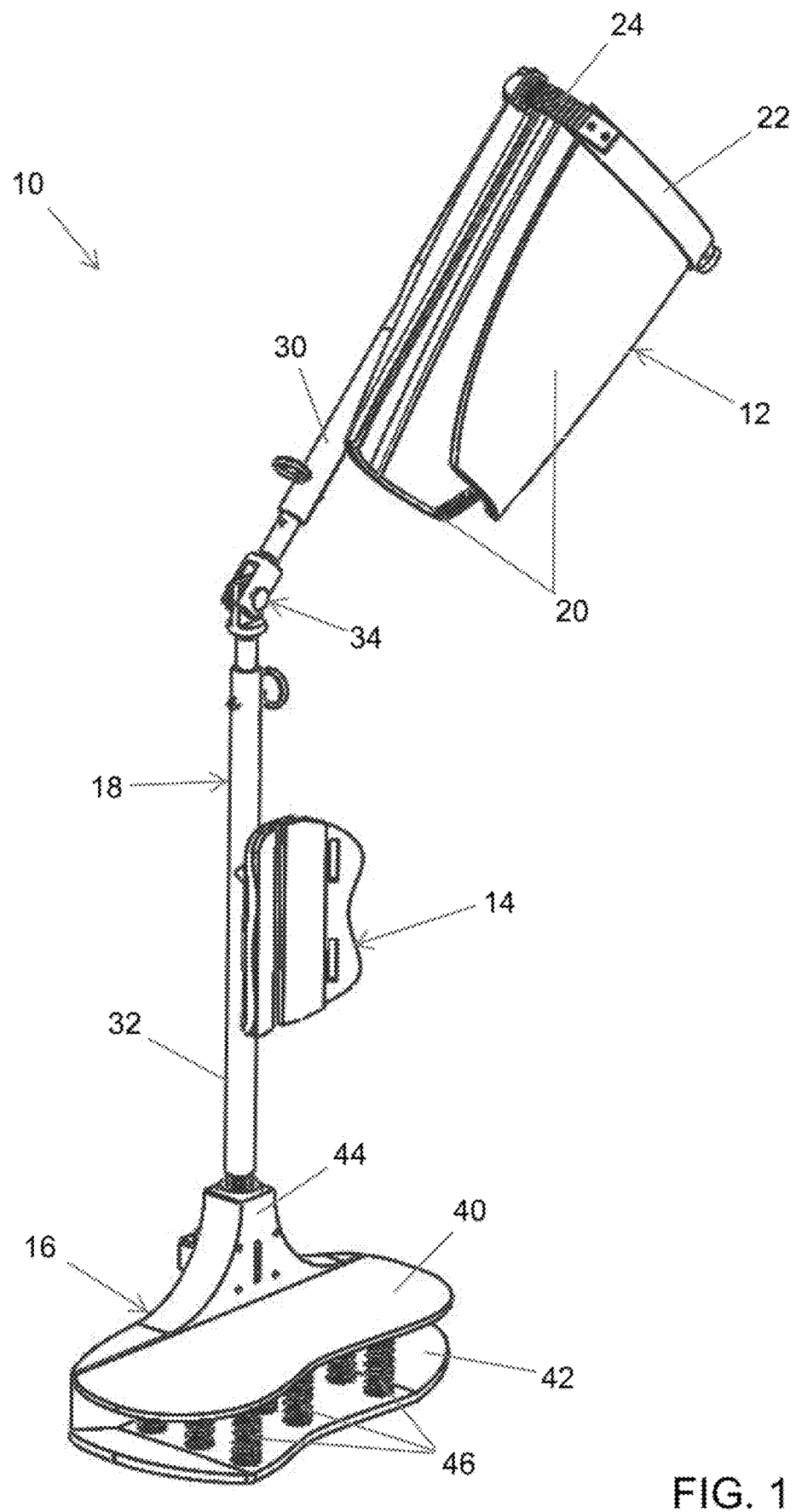
FIGS. 1 and 2 are isometric and side views representing an assistive movement device in accordance with a nonlimiting first embodiment of this invention.
Figure 2:
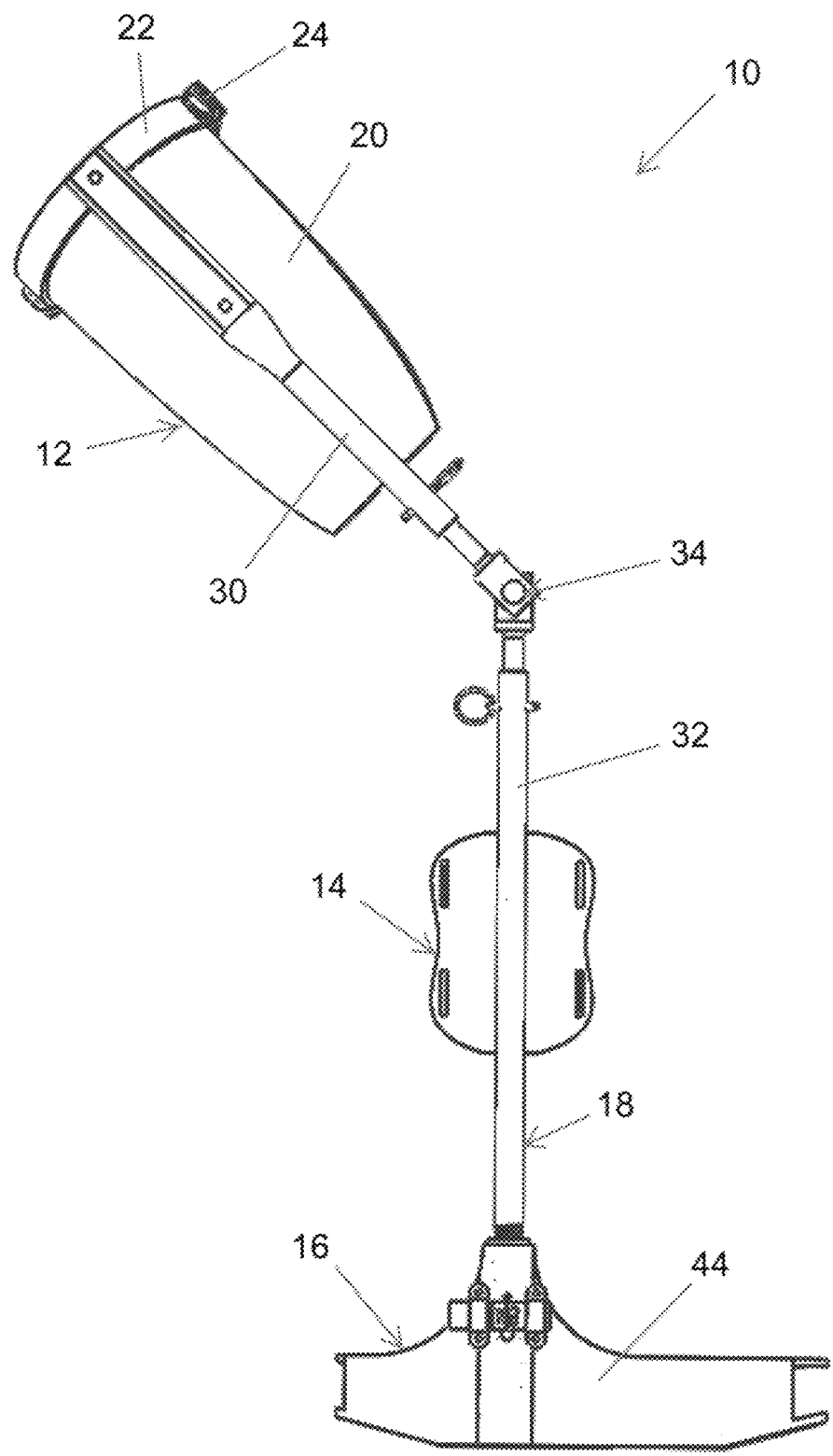
Figure 3:
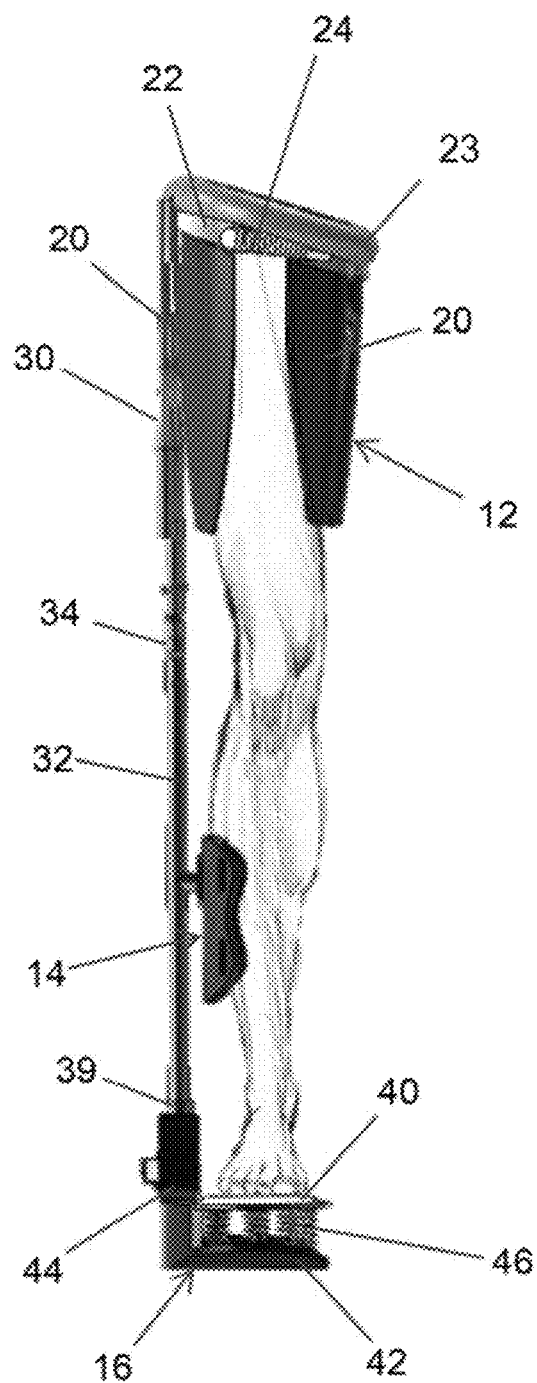
FIG. 3 is a front view of the assistive movement device of FIG. 1 secured to a human leg.

FIGS. 1 through 13 represent a first nonlimiting embodiment of an assistive movement device 10. The device 10 includes an upper attachment 12, a lower attachment (e.g., a lower leg guard 14 in the embodiment illustrated in the drawings), and a base 16, all of which are functionally coupled to one another with a frame assembly 18. An individual recovering from an injury below their knee may secure the device 10 to the injured leg with suitable attachments means associated with the upper attachment 12 and lower leg guard 14, for example, as represented in FIG. 3. The device 10 is primarily secured around the individual's upper thigh with the upper attachment 12. While the individual is standing, walking, or otherwise applying their weight on the leg, an adjustable portion of their weight (load) can be redirected from the base 16 through the frame assembly 18 and concentrated around the individual's hip/pelvic region at the upper attachment 12. A knee joint 34 of the frame assembly 18 preferably has a pivoting axis that is substantially aligned with the transverse axis of the user's knee that permits flexion and extension, and allows for full range of motion (e.g., along a single axis of pivoting between fully extended to a straight leg (due to extension motion) and fully bent at the knee (due to flexion motion), for example, in a posterior direction when standing) in both weight bearing and non-weight bearing situations. This allows the user to maintain mobile independence as close to a normal lifestyle as possible during the healing process.

Figure 4:
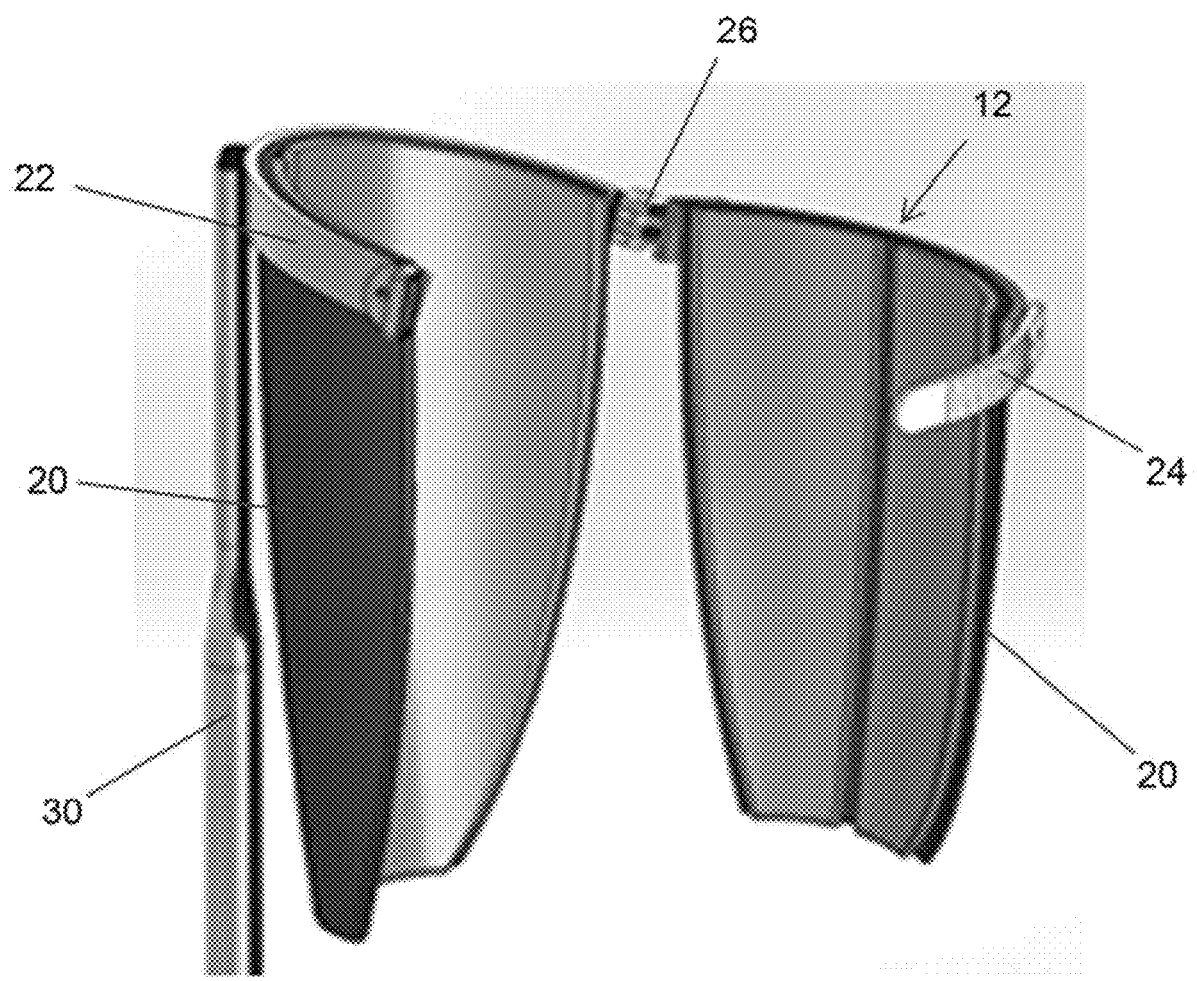
FIG. 4 is a detailed view of an upper attachment of the assistive movement device of FIG. 1 in an open position.

In the nonlimiting embodiment shown in the drawings, the upper attachment 12 includes a pair of side panels 20, a hip ring 22, and a ratchet mechanism 24. Each of the side panels 20 is formed of a rigid exterior panel having a padding on an interior thereof intended to contact the user's leg. The side panels 20 are shown pivotally connected to one another in a clamshell configuration. In the embodiment of FIG. 4, this pivot connection is provided by a hinge 26 (FIG. 4) at the hip ring 22, such that one of the side panels 20 (e.g., adapted for being located inside of the leg) may swing away from the other side panel 20 (e.g., secured to the frame assembly 18) and thereby open the upper attachment 12 to promote ease of attachment to the user's leg. By opening in this manner rather than being fixed in a closed position, the user is not required to insert their foot into the hip ring 22 and slide the device 10 along the injured leg into position. By allowing the side panels 20 to pivotally open as represented in FIG. 4, the user can position the device 10 against their leg with one hand and close the side panels 20 with the other hand and thereby reduce the likelihood of aggravating the injured area.

Figure 5:
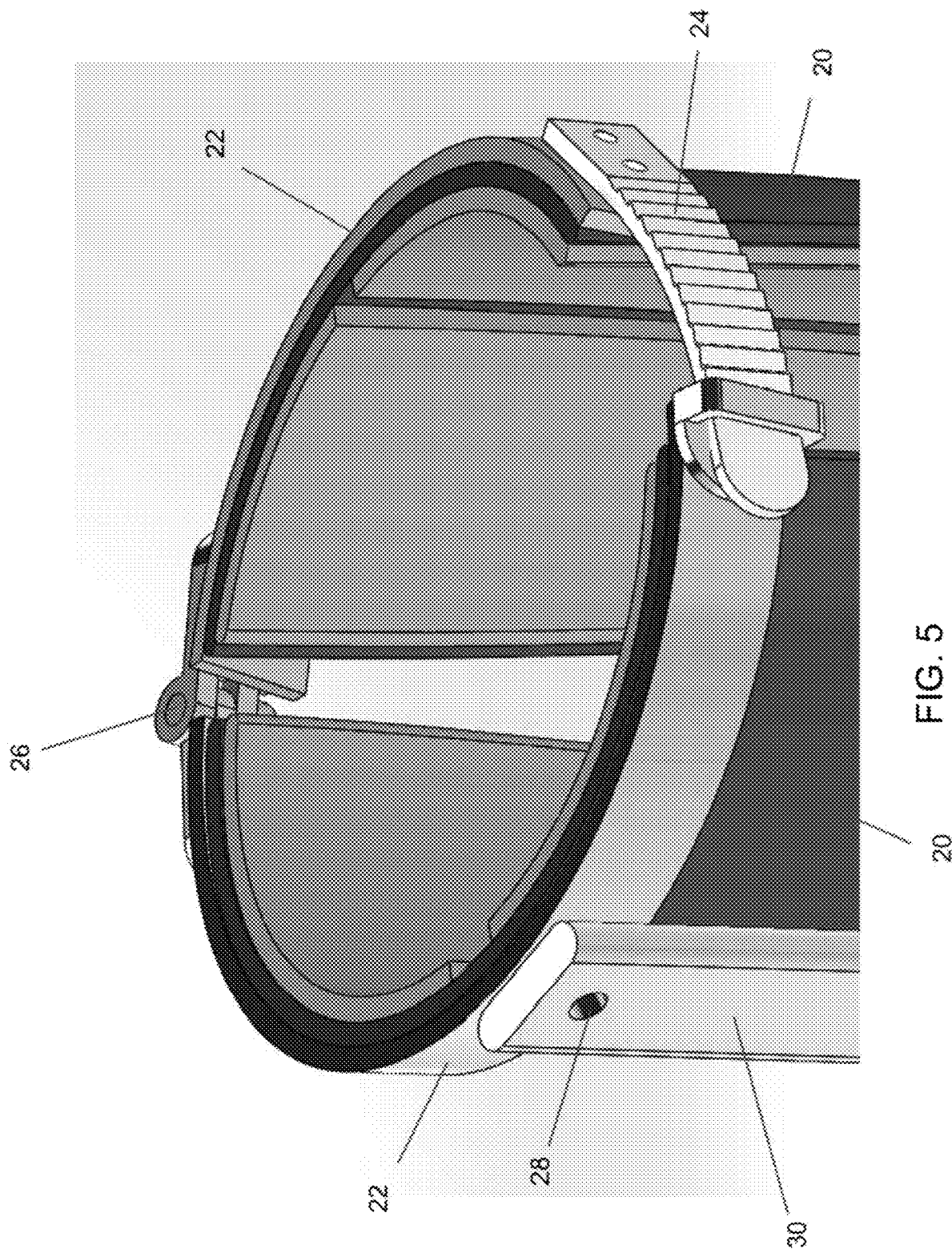
FIG. 5 is a detailed view of a ratchet mechanism of the upper attachment of FIG. 4.

Once closed around the user's thigh, the side panels 20 may be secured in the closed position with the ratchet mechanism 24, best shown in FIG. 5. Preferably, the ratchet mechanism 24 is slidably adjustable such that the inner diameter of the hip ring 22 is selectively adjustable, thereby allowing the device 10 to accommodate a wide array of users having varying size thighs and enabling each individual user to choose a tightness that they are comfortable with during use of the device 10. The hip ring 22 may optionally be padded with a compressible material 23 (e.g., foam) to promote user comfort, as represented in FIG. 3. FIG. 5 represents the hip ring 22 as comprising a through-hole 28 suitable for a pin connection (not shown) or other structure suitable for rotatably securing the hip ring 22 to an upper side bar (member) 30 of the frame assembly 18. Preferably, the upper attachment 12 is rotatable relative to the upper side bar 30 in order to promote the ability of the frame assembly 18 to conform to the natural movements of the injured leg. This optional, but preferred, aspect of the invention is believed to promote the comfort and assistive healing efficacy of the device 10.

Figure 6:
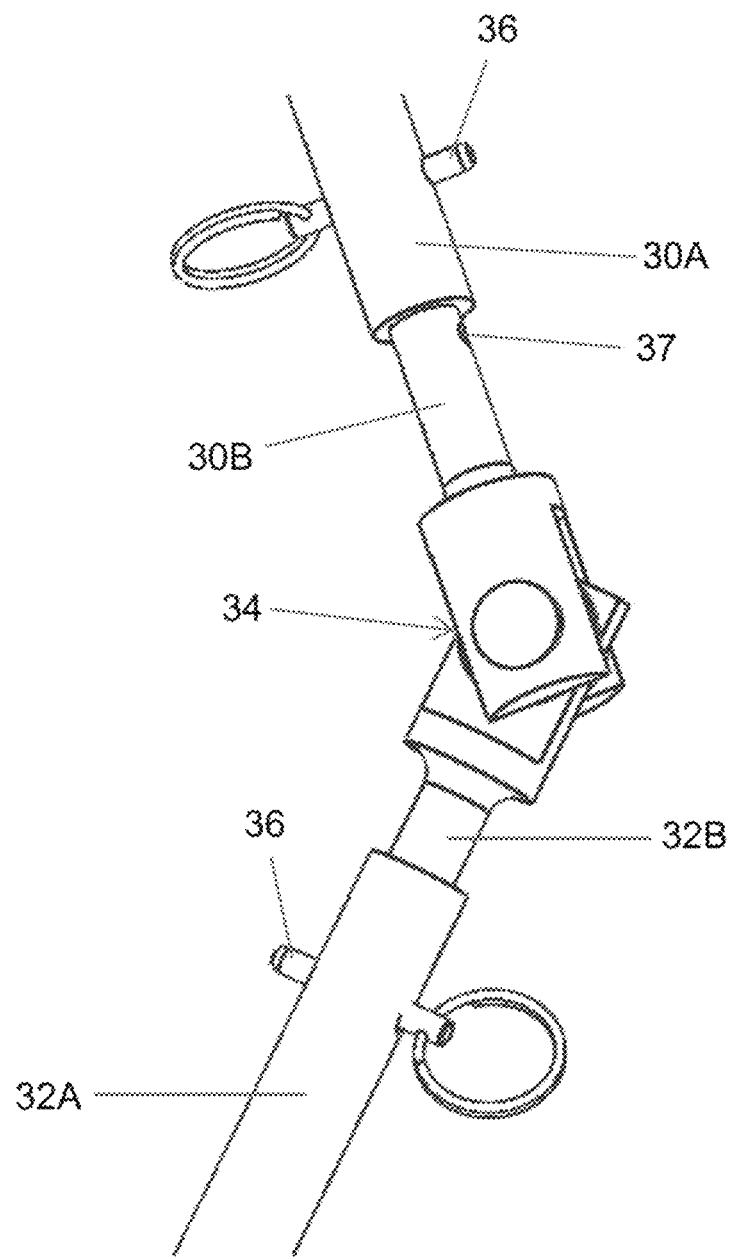
FIG. 6 is a detailed view of a knee joint of the assistive movement device of FIG. 1.

In addition to the upper side bar 30, the frame assembly 18 includes a lower side bar (member) 32 pivotally secured to the upper side bar 30 at the knee joint 34. The upper and lower side bars 30 and 32 are preferably rigid members capable of resisting bending when subjected to the full weight of an individual wearing the device 10. Although not required, the knee joint 34 is preferably a revolute joint having a single-axis of rotation, as best shown in FIG. 6. A revolute joint is believed to be preferred over a typical single pin joint because a revolute joint promotes distribution of shear forces. While a revolute joint may be more susceptible to bending moments, improved shear force resistance is believed to be of greater importance as a majority of the human gait cycle involves placing the knee joint 34 in shear loading. In contrast to other movement assistance devices that do not allow the user to bend their knee, the knee joint 34 of the device 10 is preferably capable of promoting a natural gait during movement. For example, relatively normal movement is possible as compared to the combination of crutches and a cast which commonly result in an "outward leg swing" when a user is moving, particularly when climbing stairs, due to the knee being fixed.

Preferably, the length of each of the side bars 30/32 is selectively adjustable in order to conform to the height of individual users. To this end, FIG. 6 represents the device 10 as having a height adjustment feature. In the nonlimiting embodiment of FIG. 6, portions 30A/30B and 32A/32B of each side bar 30/32 are telescopically slidable relative to one another and selectively secured to each other with a pin 36, which can be inserted in any one of several holes 37 located along the length of each side bar 30/32.

Figure 7:
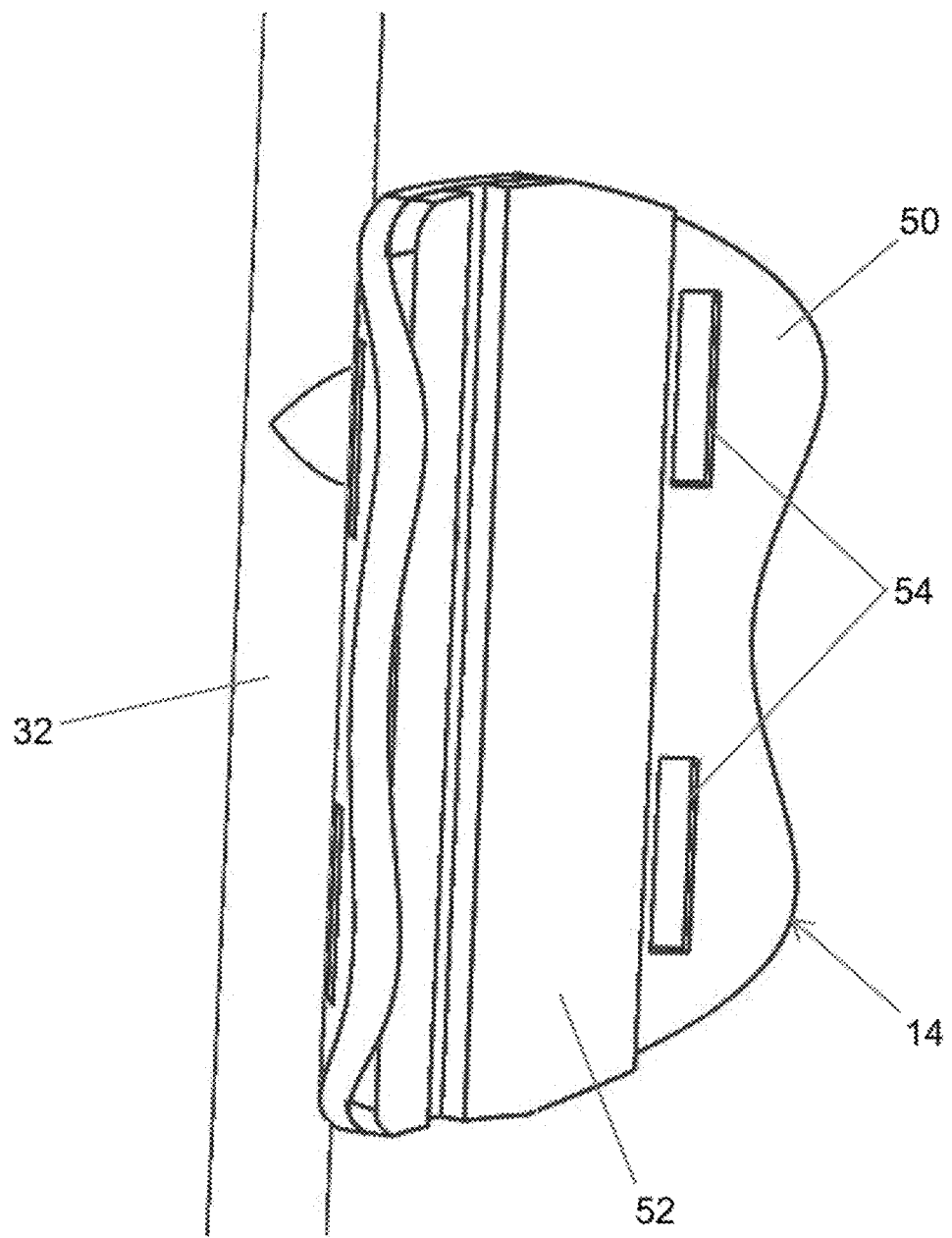
FIG. 7 is a detailed view of a lower leg guard of the assistive movement device of FIG. 1.
Figure 8:
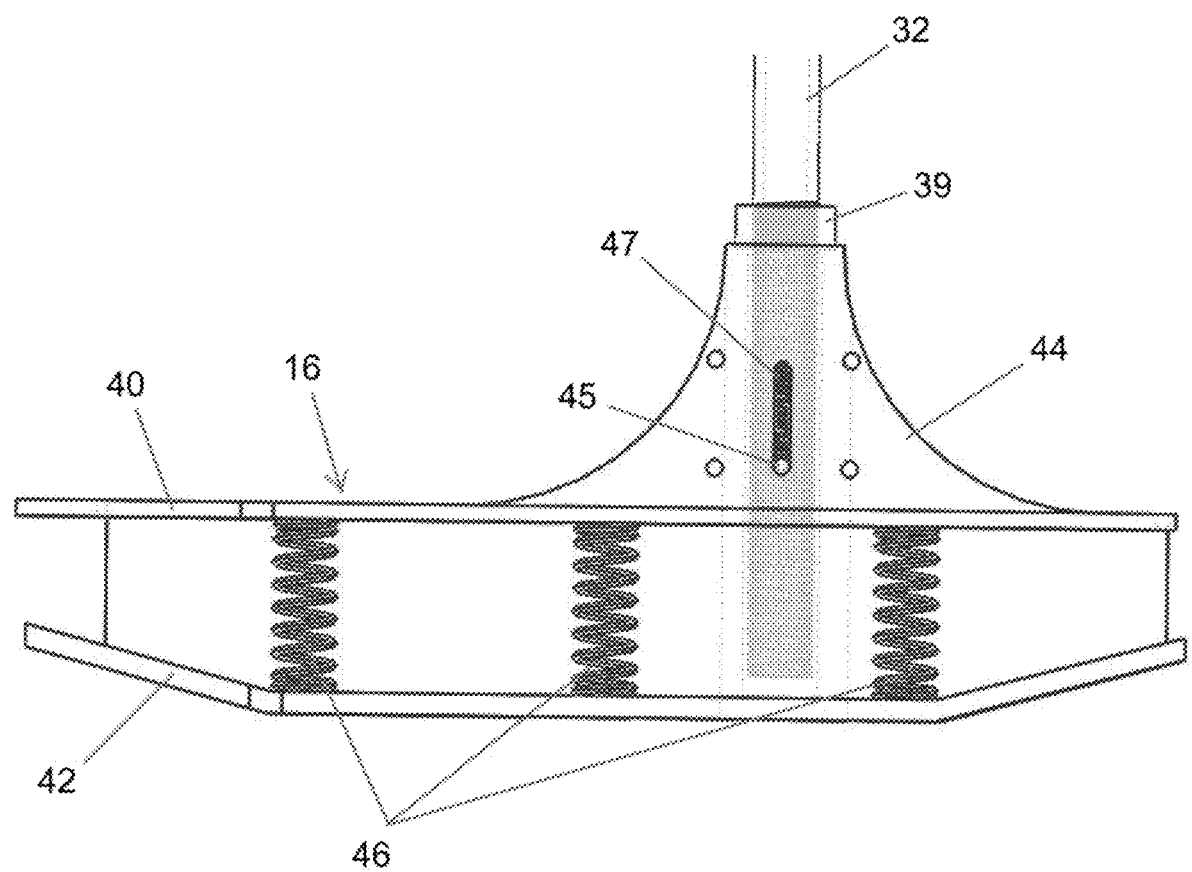
FIG. 8 is a detailed side view of a base of the assistive movement device of FIG. 1, with a base plate thereof represented as partially transparent to provide a view of internal features and components of the base.

The lower leg guard 14 is represented in the illustrated embodiment as secured to the lower side bar 32 in a fixed position. The lower leg guard 14 includes a curved outer rigid panel 50 having padding 52 on the concave side thereof, as best shown in FIG. 7. Slots 54 are formed in the lower leg guard 14 for insertion of retaining straps (not shown). A user may place an outer portion of their shin and/or calf against the padding 52 of the lower leg guard 14 and use the straps to secure the device 10 to their lower leg. Preferably, the lower leg guard 14 is configured to only exert a relatively small radial force against an individual's lower leg sufficient to retain the leg against the device 10. Preferably, all or substantially all longitudinal forces applied to the frame assembly 18 are distributed to the user at the upper attachment 12 rather than the lower leg guard 14 to reduce the likelihood of aggravating the injury. Since the only other point of attachment to the user above the lower leg guard 14 is the upper attachment 12, all portions of the device 10 below the knee joint 34 are able to freely dangle and pivot as desired, thereby reducing the likelihood that the device 10 will adversely affect the user's normal gait.

The base 16 (FIGS. 8 and 9) includes a base plate 42 rigidly secured to a base block 44 that is coupled to a distal end of the lower side bar 32. A foot plate 40 is coupled to an upper portion of the base plate 42 with means that enables the foot plate 40 to be resiliently moved toward the base plate 42. In the nonlimiting embodiment illustrated in the drawings, a suitable means is illustrated as comprising multiple helical compression springs 46 that serve as means for biasing the foot plate 40 upward and away from the base plate 42. As represented in FIG. 3, during operation the device 10 is attached to the user such that the user's foot rests on an upper portion of the foot plate 40. During use, the springs 46 promote an even load distribution across the foot plate 40. The springs 46 are configured to allow the user to place a controlled force on the bottom of their foot and through the injured portion(s) of the leg. Preferably, the springs 46 are surrounded by a foam or other compressible material (not shown) in order to protect and retain the springs 46 in position. Preferably, the foam's equivalent spring constant is sufficiently low that it will not affect the force on the user's leg. A cover (not shown) may be located between and along edges of the foot plate 40 and base plate 42 to protect and retain the foam and springs 46 therebetween. Preferably, the cover and its seal to the base plate 42 and foot plate 40 are water tight. The cover may be formed of various materials including but not limited to elastomers.

A lower surface of the base plate 42 may include treads (not shown) in order to reduce the likelihood of slipping during movement. The base plate 42 is preferably curved or angled at the front (anterior) and back (posterior) (relative to the user's foot) of the base plate 42 to allow the user to roll their foot from back to front (much like during normal gait heel-touch and toe-off) while walking without actually angling their foot (which could be harmful to ankle injuries).

To provide a variable load function, the base block 44 is preferably coupled to the lower side bar 32 such that the base block 44 and lower side bar 32 move, translate, or reciprocate relative to each other. In the embodiment represented in the drawings, a slide-coupling is represented by the lower side bar 32 telescoping into a bore within the base block 44. In order to control the relative displacement between the lower side bar 32 and the base plate 42 and base block 44 of the base 16 during use of the device 10, an adjustment collar 39 (best shown in FIG. 10) may be threadably coupled to the lower side bar 32 directly above an upper portion of the base block 44. By controlling the relative displacement between the lower side bar 32 and base block 44, the relative distance between the foot plate 40 and base plate 42 is controlled to limit the force applied to the individual's foot via the compression springs 46. In this configuration, the load applied to the user's leg while standing and/or walking can be adjusted and controlled by the extent (distance) to which the lower side bar 32 is able to slidably travel relative to the base block 44 toward the base plate 42 before the adjustment collar 39 contacts the rigid base block 44. Preferably, the lower side bar 32 and base block 44 are slidably adjustable relative to each other to an extent that the individual's foot receives no amount of force from the load, the entire force from the load, or any amount of force therebetween when standing or walking. As used herein, the "entire force from the load" (or simply, the "entire load") refers to an amount of force that would be applied to the foot from the load due to standing or walking under normal conditions without use of an assistive movement device.

Preferably, if the adjustment collar 39 is rotated to an uppermost position on the lower side bar 32, a maximum displacement between the base block 44 and the lower side bar 32 is possible and the entire load caused by the user's movement may be applied to the user's foot. In contrast, if the adjustment collar 39 is rotated to a lowermost position in which the collar 39 contacts the base block 44 (FIG. 8), no displacement will occur between the base block 44 and the lower side bar 32 and the device 10 will preferably redirect the entire load caused by the user's movement to the upper attachment 12 and little or no load will be applied through the user's lower leg to the user's foot. By rotating the adjustment collar 39 to a specific longitudinal position along the lower side bar 32 between the uppermost and lowermost positions, the user may selectively control the amount of force applied to the injured leg during movement. For example, the adjustment collar 39 may be configured to increase in increments of thirty pounds for every thirty degrees rotated. Preferably, load increments, load percentage, or other scale markings are displayed on the adjustment collar 39, lower side bar 32, base block 44, or other convenient location.

Figure 11:
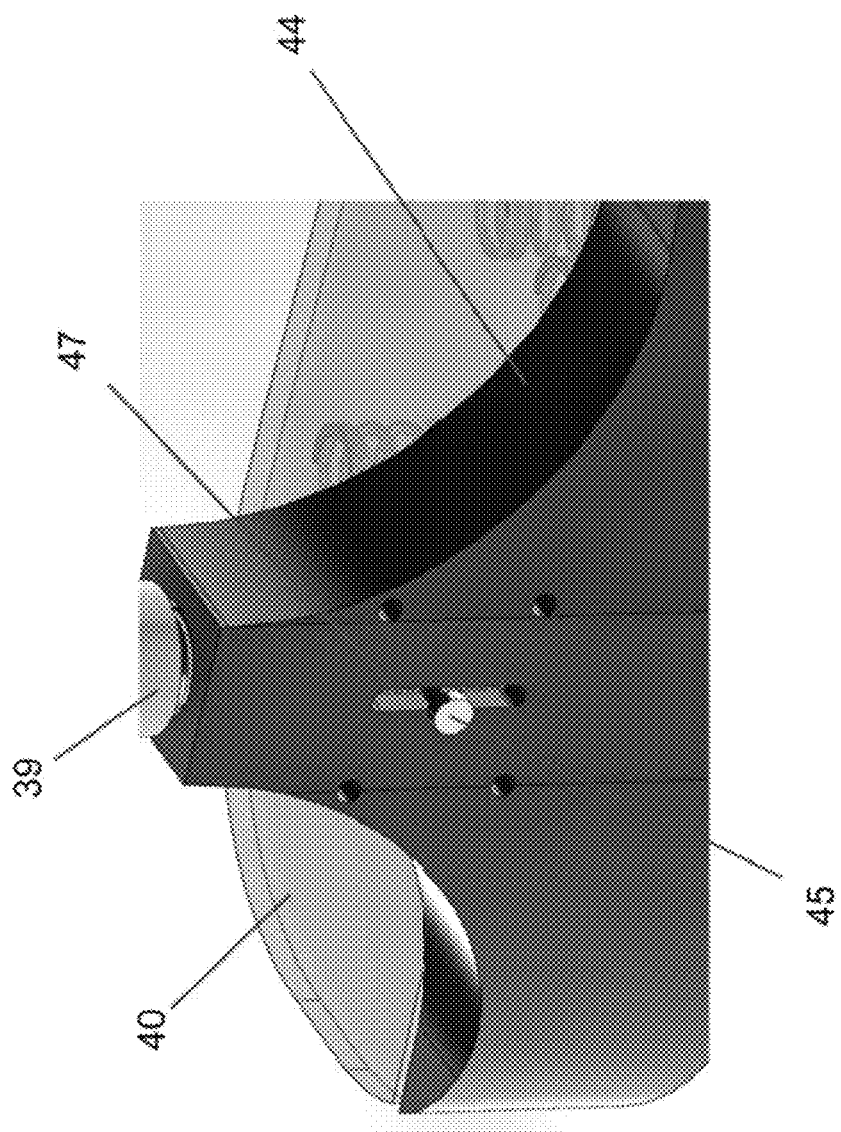
FIG. 11 is a detailed view of a pin-and-slot constraint of the assistive movement device of FIG. 1.

To retain the base block 44 on the lower side bar 32 and constrain the relative movement therebetween, FIG. 11 represents the lower side bar 32 as comprising a pin 45 radially extending therethrough and slidably engaging a slot 47 in the base block 44. The slot 47 is elongated in a direction parallel to the longitudinal axis of the lower side bar 32. When the frame assembly 18 is pulled upwards as the user lifts up the injured leg, the pin 45 will move upwards towards the top of the slot 47 and serves to lift the base 16 once the pin 45 reaches the top of the slot 47 and engages a stop effectively defined by the uppermost extent of the slot 47. In such a configuration, the pin 45 preferably extends through oppositely disposed sides of the base block 44 such that the weight of the base 16 is evenly distributed.

Preferably, the pin 45 engages the stop at the uppermost extent of the slot 47 when the lower side bar 32 is withdrawn from the base plate 44 to its maximum extent. In practice, this may be achieved by having the user set the device 10 to their height by using the height adjustment feature of the side bars 30/32, discussed above in reference to FIG. 6. When a force is applied to the foot plate 40, the pin 45 will preferably be displaced downward toward a bottom of the slot 47 and there will be little or no load redirected by the frame assembly 18 until the adjustment collar 39 contacts the base block 44.

Figure 9:
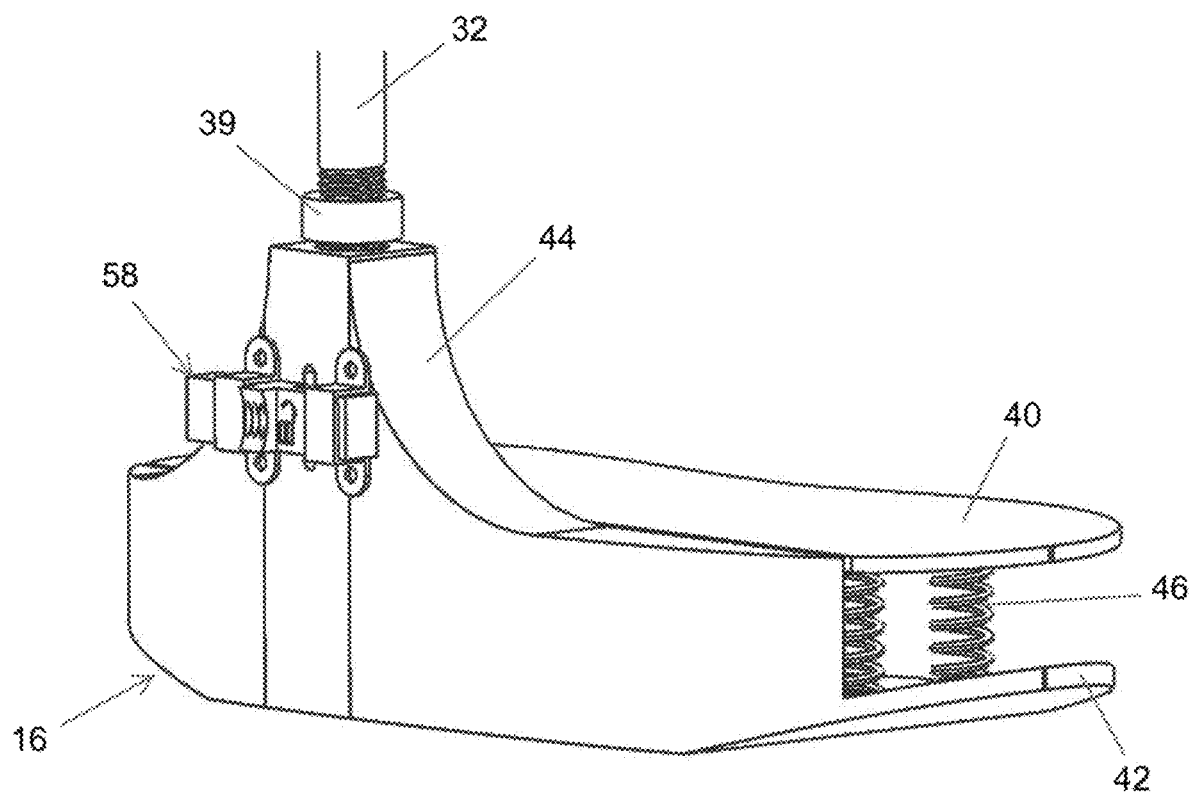
FIG. 9 is a detailed perspective view of the bach of the base of FIG. 8.
Figure 10:
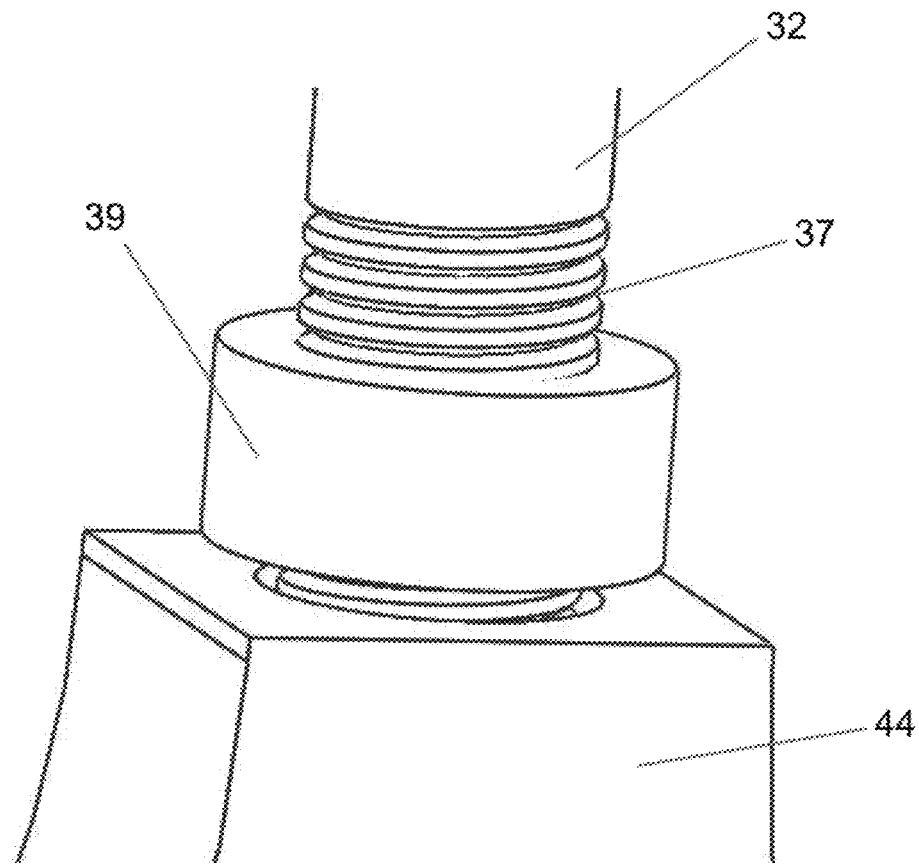
FIG. 10 is a detailed view of an adjustment collar of the assistive movement device of FIG. 1.

In addition to the above functionality, it is foreseeable and within the scope of the invention that the pin 45 may be used in conjunction with markings on the base block 44 to indicate load increments, load percentage, or other scale markings suitable for identifying the amount of the load that will be applied to the user's injured leg when walking or standing. Optionally, the base 16 may include a cover or a locking device that permanently or removably covers the pin 45. FIG. 9 represents a nonlimiting locking device 58 configured to keep the pin 45 in a fixed position, for example, such that the adjustment collar 39 remains in contact with the base block 44 and ensures that a load will not be applied to the user's lower leg.

Figure 12:
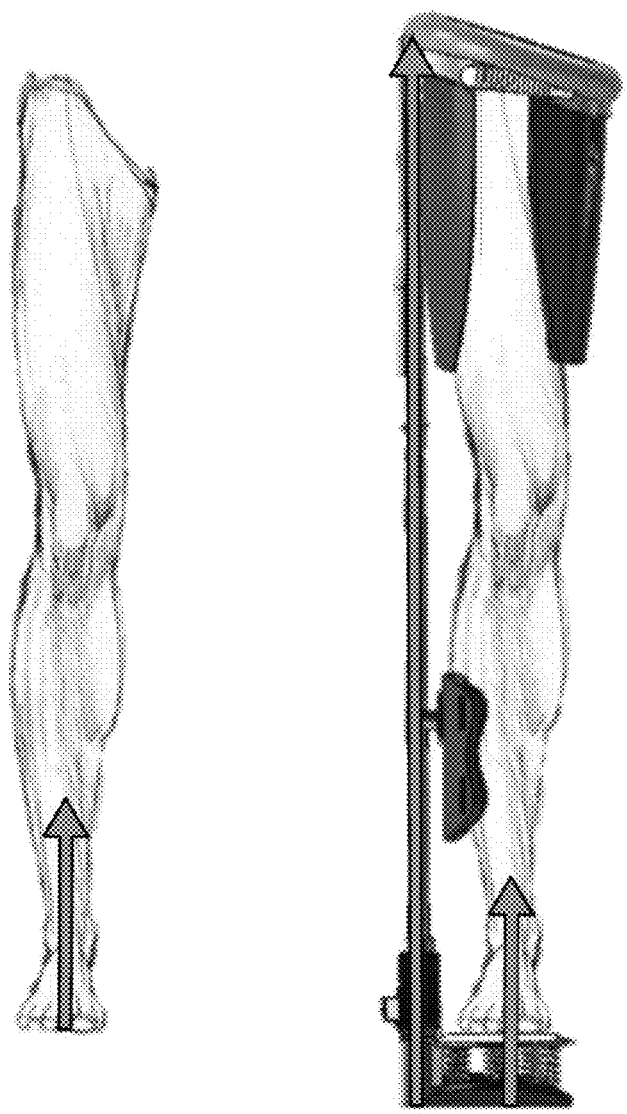
FIG. 12 schematically represents loading paths that exist when walking on an unassisted leg (left) and a leg assisted by the assistive movement device of FIG. 1 (right).

During rehabilitation, the user may begin recovery with the adjustment collar 39 located at the lowermost position, and thereafter may periodically move the adjustment collar 39 vertically upwards relative to the threads 37 on the lower side bar 32 as the injury heals, gradually increasing the amount of load on the leg until the injured leg is strong enough to bear all of the weight when walking. During movement, the springs 46 compress and allow the user to feel the force resulting from their weight (load) until the adjustment collar 39 contacts the base block 44. Once the adjustment collar 39 contacts the base block 44, all remaining force for that step is preferably redirected away from the user's foot by the device 10, and instead is transmitted from the base block 44 to the upper attachment 12 through the frame assembly 18. Consequently, the higher the adjustment collar 39 is located on the lower side bar 32, the larger the gap between the adjustment collar 39 and the base block 44 will be and the more the user can compress the springs 46 before the device 10 redirects the remaining force. FIG. 12 schematically illustrates nonlimiting exemplary load distribution to an unassisted leg (left) and a leg secured to the device 10 (right). Preferably, the device 10 distributes a selected amount of the load due to the user's weight from the base block 44 to the upper attachment 12 through the frame assembly 18 and to the hip.

Figure 13:
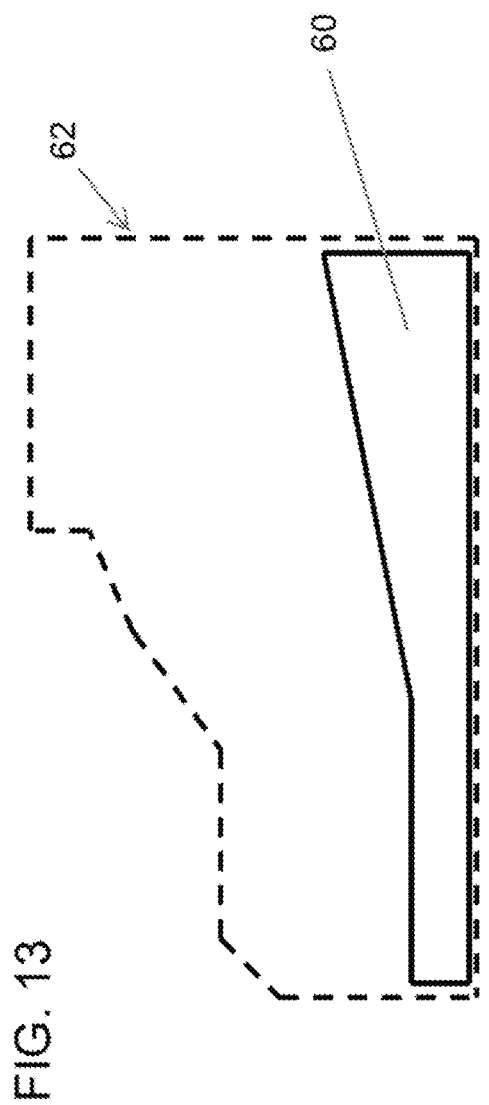
FIGS. 13 and 14 schematically represent nonlimiting embodiments of supports for use under a user's uninjured leg in order to negate the additional height resulting from the use of the assistive movement device of FIG. 1.
Figure 14:
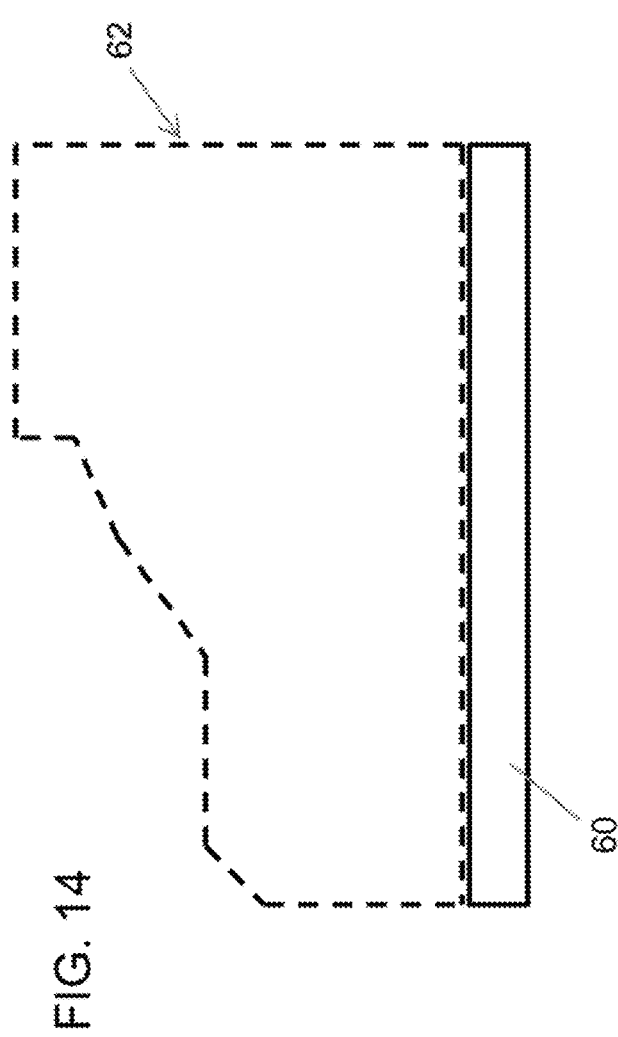

Since the springs 46, foam, treads 43, and plates 40/42 are located below the user's foot, the user's injured leg will likely be located vertically higher or raised relative to their other uninjured leg. Misalignment of the hips over time caused by this uneven height could lead to Iliotibial band syndrome (ITB), Achilles tendonitis, and/or back injuries. Therefore, a support 60 may be provided for use under the user's uninjured leg in order to negate the additional height. For example, the support may include a fitted insole with a heel that the user can place inside a shoe 62 worn on the user's foot of the uninjured leg as represented in FIG. 13, or may include a body configured to be secured to a bottom of the shoe 62 worn on the user's foot of the uninjured leg as represented in FIG. 14. The support may be formed of any material such as but not limited to a silicone rubber material.

As an alternative to the embodiment illustrated in the drawings, it is foreseeable that the function of the springs 46 under the foot plate 40 could be performed with other types of biasing means, for example, tension springs alongside the leg to reduce load. Such configuration may reduce the additional height under the user's injured leg resulting from the presence of the springs 46. It is further foreseeable that the frame assembly 18 could include additional support members located on an inner side of the individual's leg in addition to the upper and lower side bars 30 and 32, or the upper attachment 12 and the lower leg guard 14 could include structures that are directly connected to one another in a manner that is functionally equivalent to the frame assembly 18, that is, in a manner that allows for pivoting of the knee and redirecting of loads from the base 16 to the upper attachment 12, such that the frame assembly as illustrated in the drawings would be unnecessary. In addition, the lower leg guard 14 may be unnecessary if the base 16 is configured to include means for securing to the individual's leg or foot, for example, if it includes a strap or boot for securing to the foot.

Figure 15:
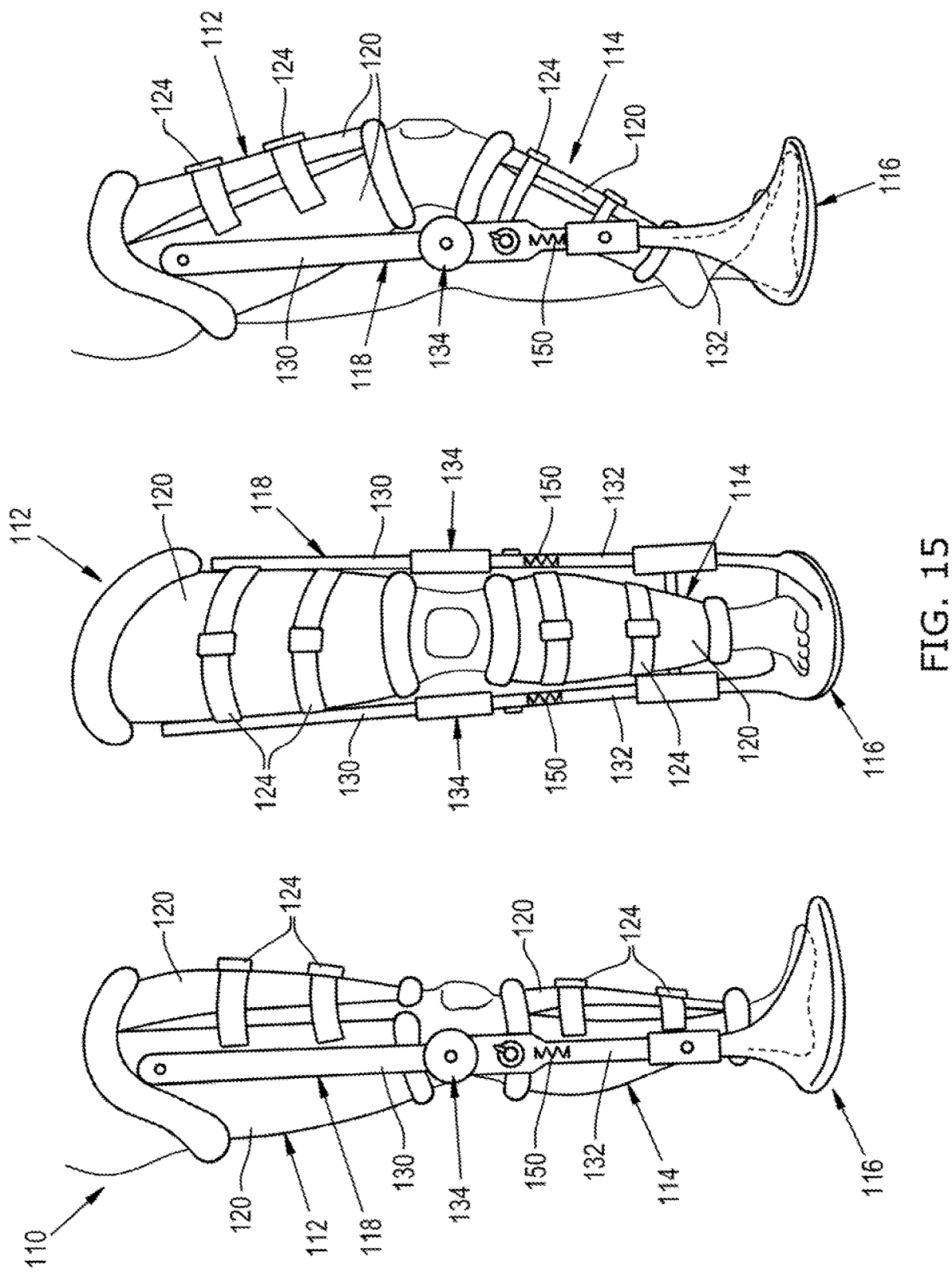
FIG. 15 includes various views representing an assistive movement device in accordance with a nonlimiting second embodiment of this invention.
Figure 16:
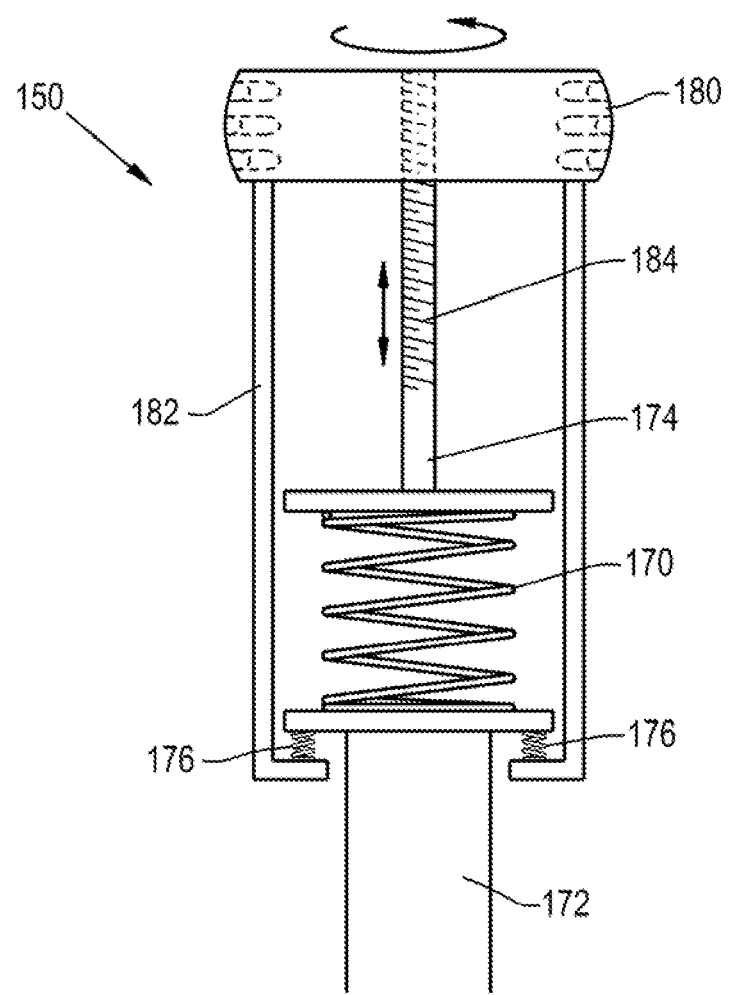
FIGS. 16 and 17 represent two alternative configurations of internal components of a biasing assembly of FIG. 15.

FIGS. 15 and 16 includes various views of a second nonlimiting embodiment of an assistive movement device 110. In FIGS. 15 and 16, consistent reference numbers are used to identify the same or functionally related elements, but with a numerical prefix (1, 2, or 3, etc.) added to distinguish the particular embodiment from the embodiment of FIGS. 1 through 14. In view of similarities between the first and second embodiments, the following discussion of FIGS. 15 and 16 will focus primarily on aspects of the second embodiment that differ from the first embodiment in some notable or significant manner. Other aspects of the second embodiment not discussed in any detail can be, in terms of structure, function, materials, etc., essentially as was described for the first embodiment.

The device 110 includes a frame assembly 118 comprising dual support via two upper members 130 and two lower members 132 coupled with a knee joint 134. Both sides of the frame assembly include a biasing assembly 150 which provides means for varying the load applied to the leg relative to the load redistributed through the frame assembly 118. Such biasing assembly 150 may include, for example, internal helical springs to allow for load variance. By including the biasing assembly 150, the distance by which the user's foot is raised above the ground by the base 116 is reduced relative to the first embodiment of FIGS. 1-14. In this embodiment, the frame assembly 118 may be coupled to the upper and lower attachments 112 and 114 such that the joint 134 pivots with and remains adjacent to the knee during use, or such that the joint 134 pivots at a different time during the user's stride than the knee as shown in FIG. 15 (far right image).

Figure 17:
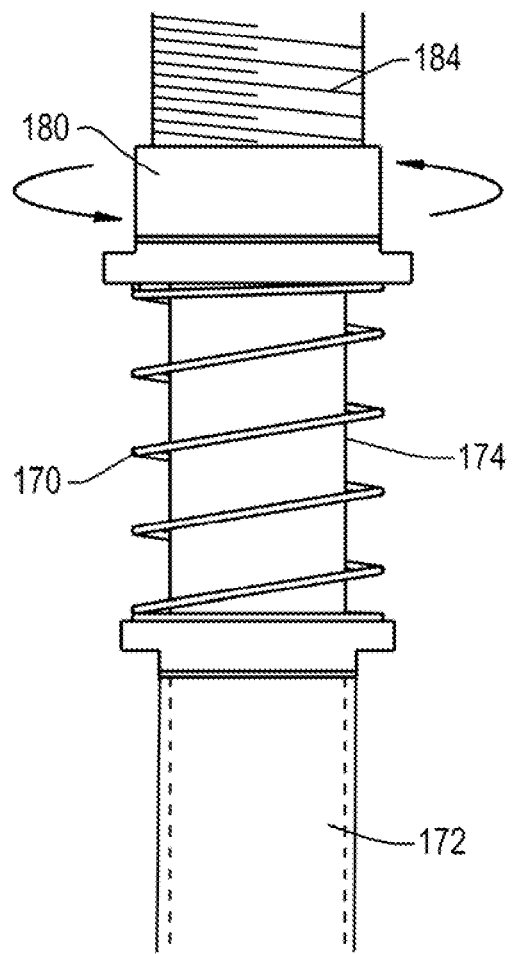

FIGS. 16 and 17 schematically represent two nonlimiting embodiments of the internal components of the biasing assembly 150. In FIG. 16, the biasing assembly 150 includes upper and lower units 174 and 172 housed at least partially within a housing 182. A spring 170 or other biasing means is located between and separates the upper and lower units 174 and 172. The housing 182 is further coupled to the lower unit via additional springs 176. While the user is walking, a load applied to the user's leg due to their weight is dependent on the distance between the upper and lower units 174 and 172. Such distance may be selected by adjusting a rotatable nut 180 which interacts with threads 184 to displace the upper unit 174 closer or farther from the lower unit 172. If the spring 170 is completely compressed, load applied to the base 116 will be redistributed through the frame assembly 118. In contrast, if the spring 170 is not fully compressed, a load on the base 116 will cause the lower member 172 to displace relative to and into the housing 182 such that at least some of the load will be directed to the user's lower leg.

FIG. 17 represents an alternative configuration of the biasing assembly 150 in which the lower member 172 includes a bore capable of slidably receiving the upper unit 174. The spring 174 surrounds the upper unit 74 and an unloaded distance between and end of the lower unit 172 and the rotatable nut 180 (e.g., the length of the spring 170 when no load is applied to base 116) may be adjusted with the rotatable nut 180 which interacts with threads 184 on the upper unit 174. If the spring 170 is completely compressed, load applied to the base 116 will be redistributed through the frame assembly 118. In contrast, if the spring 170 is not fully compressed, a load on the base 116 will cause the lower member 172 to displace relative to and receive the upper unit 174 such that at least some of the load will be directed to the user's lower leg.

Another notable difference of the second embodiment includes panels 120 of the upper and lower attachments 112 and 114 that are secured in a closed position with straps 124.

In view of the above, the device 10 provides a means for hands-free movement for an individual recovering from a lower leg injury (below the knee) that allows the user to walk with a substantially normal gait. In addition, the device 10 preferably provides the user with the ability to selectively adjust the load applied to the lower leg while walking and standing. Therefore, devices as described herein are believed to provide improved maneuverability and reduce recovery time relative to conventional post-injury movement assistance devices such as crutches.

While the invention has been described in terms of specific or particular embodiments, it is apparent that other forms could be adopted by one skilled in the art. For example, the device 10 and its components could differ in appearance and construction from the embodiments described herein and shown in the drawings, functions of certain components of the device 10 could be performed by components of different construction but capable of a similar (though not necessarily equivalent) function, and various materials could be used in the manufacturing of the device 10 and its components. In addition, the invention encompasses additional or alternative embodiments in which one or more features or aspects of different disclosed embodiments may be combined. Accordingly, it should be understood that the invention is not limited to any embodiment described herein or illustrated in the drawings. It should also be understood that the phraseology and terminology employed above are for the purpose of describing the illustrated embodiments, and do not necessarily serve as limitations to the scope of the invention. Therefore, the scope of the invention is to be limited only by the following claims.

The invention claimed is:

1. An assistive movement device for attachment to a foot and a thigh of a leg of an individual so that a load from a surface on which the individual is standing or walking is adjustably redirected from the foot of the individual to a hip of the individual instead of a lower leg of the leg of the individual, the assistive movement device comprising:
   a frame assembly comprising an upper member, a lower member, and a pivoting joint therebetween;
   an upper attachment secured to the upper member and having means for securing the upper member to the thigh of the individual;
   a base secured to a distal end of the lower member oppositely disposed from the joint and being configured to support the foot of the individual, the base having a lower surface configured to contact the surface on which the individual is standing or walking to receive the load from the surface on which the individual is standing or walking, the base having an upper portion configured to support the foot of the individual, the base and the lower member being slidably coupled so that the base and the lower member translate relative to each other in a longitudinal direction of the lower member; and
   means for adjusting the translating of the lower member and the base relative to each other to selectively enable the foot of the individual to receive any amount of the load, including no amount of the load and all of the load, when the individual is standing or walking, wherein any of the load not received by the foot of the individual is transmitted from the base through the frame assembly and through the upper attachment to the thigh of the individual and not to or through the lower leg of the individual.

2. The assistive movement device of claim 1, further comprising a lower leg guard secured to the lower member for exerting only a radial force to a portion of the leg below a knee thereof.

3. The assistive movement device of claim 1, wherein the adjusting means comprises a collar threaded onto the lower member and a base plate of the base, the assistive movement device further comprising a slot in the base plate and a pin coupled to the lower member and received in the slot to limit the translating of the lower member and the base relative to each other.

4. The assistive movement device of claim 1, wherein lengths of the upper member and the lower member are adjustable.

5. The assistive movement device of claim 1, wherein the upper attachment is rotatably secured to the upper member.

6. The assistive movement device of claim 1, wherein when the assistive movement device is secured to the individual, a pivoting axis of the joint is aligned with the knee of the leg.

7. The assistive movement device of claim 1, wherein the base comprises a base plate forming the lower surface configured to contact the surface on which the individual is standing or walking, a foot plate coupled to the base plate and forming the upper portion of the base configured to support the foot of the individual, and biasing means distributed between the foot plate and the base plate for biasing the foot plate upward and away from the base plate and evenly distributing the load across the foot plate.

8. The assistive movement device of claim 7, wherein the biasing means comprises compression springs between the foot plate and the base plate.

9. The assistive movement device of claim 1, wherein the base and the upper attachment position the frame assembly on only an outside of the leg of the individual.

10. The assistive movement device of claim 1, wherein the upper attachment comprises at least two panels configured to be located in open and closed positions, a first of the two panels being coupled to the upper member and a second of the two panels being pivotally connected to the first panel, the at least two panels securing the upper member to the thigh when in the closed position.

11. A system comprising the assistive movement device of claim 1, wherein when the assistive movement device is secured to the individual, portions of the base are located below the foot and raise the foot above the surface that the individual is standing or walking on by a dimension, the system comprising a support device that is separate from the assistive movement device and being configured to be located below a second foot on a second leg of the individual and raise the second foot above the surface that the individual is standing or walking on by the dimension.

* * * * *